United States Patent [19]

Corti et al.

[11] Patent Number: 4,490,536
[45] Date of Patent: Dec. 25, 1984

[54] SALT FREE PHOSPHOBETAINES

[75] Inventors: Miguel Corti, Hawthorne; Raymond L. Mayhew, Summit, both of N.J.

[73] Assignee: Mona Industries, Inc., Paterson, N.J.

[21] Appl. No.: 512,757

[22] Filed: Jul. 11, 1983

[51] Int. Cl.$^3$ ............................................. C07F 9/65
[52] U.S. Cl. .................................................. 548/112
[58] Field of Search ........................................ 548/112

[56] References Cited

U.S. PATENT DOCUMENTS 4,215,064 7/1980 Lindemann et al. ............ 548/112 X
4,283,542 8/1981 O'Lenick et al. ..................... 548/112

*Primary Examiner*—Richard L. Raymond
*Attorney, Agent, or Firm*—Felfe & Lynch

[57] ABSTRACT

A phosphobetaine compound of the formula

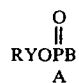

wherein
A is selected from OH, OM and OYR
B is selected from OH and OM
R is an imidazoline reactant moiety of the formula

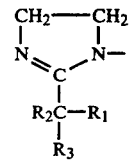

Wherein
$R_3$ is alkyl, alkenyl, alkoxy, hydroxyalkyl or hydroxyalkenyl or from $C_2$–$C_{20}$ carbon atoms each or aryl or akylaryl or cycloaliphatic of up to 20 carbon atoms.
$R_1$ and $R_2$ are individually selected from hydrogen, propionic acid, propionitrile, propionamide, propionate esters of $C_1$–$C_{12}$ alkyl, alkylaryl or alkylcycloaliphatic or alkali metal or alkaline earth metal salts or amine salts of propionic acid with the proviso that when $R_1$ is hydrogen $R_2$ must be a propionate derivative.
Y is alkylene of 2 to 6 carbon atoms optionally interrupted by up to 3 oxygen atoms, of up to 12 carbon atoms.
M is selected from alkali metals, alkaline earth metals and amines.

23 Claims, No Drawings

SALT FREE PHOSPHOBETAINES

BACKGROUND OF THE INVENTION

The present invention relates to the novel compositions of matter consisting of specific betaine derivatives referred to hereinafter as phosphobetaines.

Application Ser. No. 965,461, now U.S. Pat. No. 4,215,064 discloses novel types of phosphobetaines possessing many unusual properties.

The products of U.S. Pat. No. 4,215,064 suffer one disadvantage, namely that they contain varying amounts of sodium chloride which is disadvantageous for many applications.

The products of this invention, on the other hand, are "salt free" and in addition to this characteristic, exhibit unusual foaming, wetting, cleansing, detergency, antistatic, viscosity building, solubilizing, emulsifying, lubricating and corrosion inhibiting properties.

THE INVENTION

The novel phosphobetaine compounds of the invention may be represented by the following general formula:

Where
A is selected from OH, OM and OYR, B is selected from OH and OM.
R is represented by an imidazoline reactant of the formula:

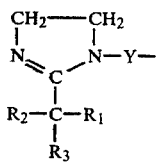

Where
R is $C_2$–$C_{20}$
$R_1$ and $R_2$ may be the same or different and may be hydrogen, propionic acid, propionitrile, propionamide, propionate esters of $C_2$–$C_{12}$ alkyl, alkylaryl or alkylcycloaliphatic, or alkali, alkali metal or amine salts of propionic acid with the proviso that when $R_1$ is hydrogen $R_2$ must be a propionate derivative.
Y may be alkylene optionally interrupted by up to 3 oxygen atoms of up to 12 carbon atoms, which alkylene chain may be optionally substituted with lower alkyl or alkoxy e.g. of not more than 10 carbon atoms.
M can be hydrogen, alkali or alkaline earth metals, amines or RY.

THE IMIDAZOLINE MOIETY

The synthesis of hydroxy substituted imidazolines is well documented in the literature and need not be reviewed here (U.S. Pat. Nos. 2,267,965 and 2,528,378). The reaction of these imidazolines with phosphorylating agents generally leads to dark brown to black products possessing poor water solubility and generally lacking in desirable surface active properties.

It has been discovered, however, that when an imidazoline is first reacted with an appropriate acrylate which may include acrylic acid, acrylamide and acrylate esters the resulting product can readily be phosphorylated to produce products with extremely interesting surface active properties.

Although the exact composition of this reaction product has not been established we believe it is essentially that indicated in the invention disclosure.

It has been found that these imidazolines can be reacted with either one or two moles of the acrylic derivative to give either a mono- or di-substituted product as follows.

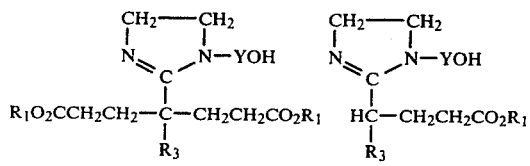

The imidazolines can be prepared from a variety of acids ranging from $C_4$–$C_{22}$. They may be normal straight chain fatty acids or acids with additional groups such as hydroxy. They may also be alkylaryl or alkylcyclo aliphatic acids.

The amines are derived from substituted 1,2-diamines. Examples of amines, but not limited to these, would be N-hydroxyethyl ethylene diamine, N-hydroxypropyl ethylene diamine, N-hydroxybutyl ethylene diamine, etc. In addition the resulting imidazolines can be alkoxylated with ethylene oxide, propylene oxide, butylene oxide etc. to yield polyalkoxylated products.

THE PHOSPHORIC ACID MOIETY

The desired products are obtained by reacting the imidazoline moiety with a phosphorylating agent to produce the phosphoric acid products of this invention.

Although there are various phosphorylating agents including phosphoric acid, polyphosphoric acid, phosphorus pentoxide and various phosphorus halides the preferred agents used in preparing the product of this invention are phosphorus pentoxide and polyphosphoric acid.

In carrying out these phosphorylations with the aforesaid agents a mixture of esters is obtained. These are mono and diesters with the relative ratios of mono to diester, being a function of the ratio of imidazoline derivative to the phosphorylating agent. Due to the strong dehydrating effects of the phosphorylating agent, products of this invention are limited to ratios of approximately 1:1 to 4:1 with the preferred ratio depending to a great extent on the end use of the product and the ratio of mono to diester desired.

In view of this, all products represent a mixture of mono and diesters as represented by the basic structures.

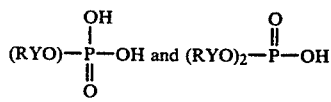

It should be noted that imidazolines per se are quite sensitive to moisture and that hydrolysis readily occurs even at room temperature. This results in formation of the open chain amino amide.

Although it would be expected that the imidazoline ring would remain intact during the acrylate reaction and the phosphorylation, hydrolysis might be expected to occur during the final reaction step.

To our suprise however this hydrolysis did not occur and the imidazoline ring remains intact as measured by ultraviolet absorption at 230–240 nanometers.

The surprising stability of this ring system would appear to account for some of the unusual properties of these products. For example these products have been found to be not only soluble but indefinitely stable in a 25% concentration of hydrochloric acid and a 40% concentration of sodium hydroxide. This is particularly unexpected since the unphosphated precursors do not exhibit this stability but rather decompose in a matter of hours to a few days.

The following examples are presented for purposes of illustration only and not to imply limitations thereof.

EXPERIMENT 1

620 grams of a hydroxy containing imidazoline prepared by reacting coconut fatty acid with hydroxyethyl ethylene diamine were charged to a 2 liter round bottom, 3-necked flask equipped with agitation, thermometer, reflux condenser and heating mantle. 348 grams of methyl acrylate was then added with good agitation followed by 32 grams of acrylic acid. The mixture was heated at 100°–110° C. for approximately four hours, or until an 85% conversion of the acrylate has occurred as determined by the analysis of unreacted acrylate. The product has the following probable structure:

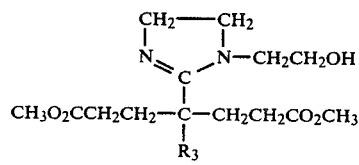

Where $R_3 = C_4-C_{16}$

This is Reactant A.

EXPERIMENT 2

894 grams of Reactant A were charged to a 2 liter, 3-necked, round bottom flask equipped with an agitator, thermometer, reflux condenser and heating mantle. To this product 106 grams of anhydrous phosphorus pentoxide was slowly added while maintaining vigorous agitation and gradually raising the temperature to 85°–100° C. After the addition is completed the temperature is maintained at 85°–100° C. for several hours to ensure completion of the reaction. The resulting product is represented by the following formula:

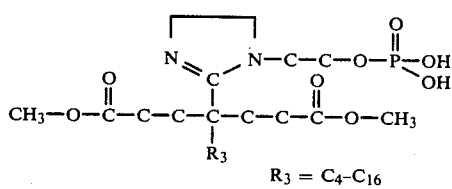

AND

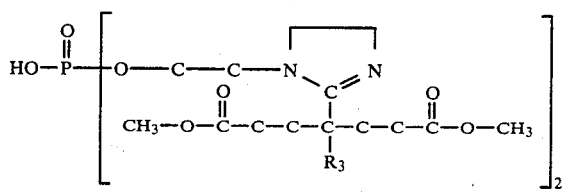

This is Reactant B.

EXPERIMENT 3

To 585 parts of water, 335 parts of reactant B and 80 parts of 50% sodium hydroxide are added under good agitation. The mixture is then heated to 85°–100° C. for 1 hour or until 1 part of product is clear in 9 parts. of 40% sodium hydroxide. The resulting product is represented by the following formula:

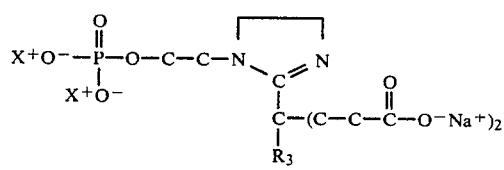

$X = H^+$ or $Na^+$      $R_3 = C_4-C_{16}$

AND

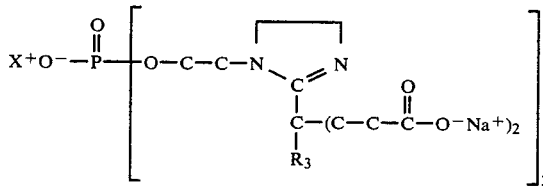

$X^- = H^+$ or $Na^+$      $R_3 = C_4-C_{16}$

EXPERIMENT 4

To 877 parts of reactant A are added 123 parts of 115% polyphosphoric acid. The mixture is then heated to 85°–100° C. for several hours until the acid values remain unchanged. This product has the following probable structure:

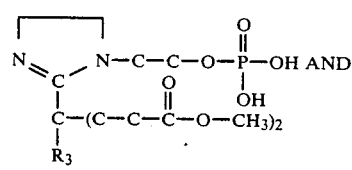

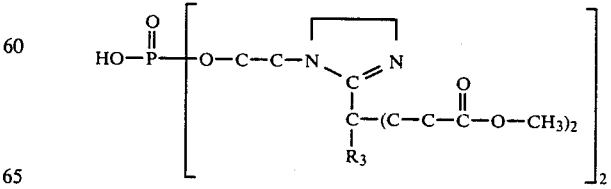

This is reactant C

EXPERIMENT 5

To 586 part of water are added 335 parts of reactant C and 78 parts of 50% sodium hydroxide under good agitation. The mixture is then heated to 85°–100° C. for a few hours until 1 part of product is clear in 9 parts of 40% sodium hydroxide. This product has the following probable structures:

$$N=C\begin{matrix}N-C-C-O-\overset{O}{\underset{\|}{P}}-O^-X^+\\ | \quad O \quad | \\ | \quad \| \quad O^-X^+ \\ C-(C-C-C-O^-Na^+)_2 \\ | \\ R_3\end{matrix}$$

$X = H^+ \text{ or } Na^+$

AND $$\left[\overset{O}{\underset{\underset{X^+O^-}{|}}{P}}-O-C-C-N\underset{C}{\diagdown}\underset{\|}{\diagup}N \atop \begin{matrix}|\\ C-(C-C-\overset{O}{\underset{\|}{C}}-O^-Na^+)_2 \\ | \\ R_3\end{matrix}\right]_2$$

$X = H^+ \text{ or } Na^+$

EXPERIMENT 6

To 762 grams of coco derived imidazoline are added 238 grams of methyl acrylate. The reactants are then heated in a suitable vessel, equipped with stirrer, thermometer, reflux condenser and heating mantles, to 90°–105° C. for four hours, or until a minimum of 85% reaction is obtained as determined by unsaturation analysis on the acrylate. This product has the following probable structure:

$$N=C\begin{matrix}N-C-C-OH \\ | \quad O \\ | \quad \| \\ HC-C-C-C-O-CH_3 \\ | \\ R_3\end{matrix}$$

Where $R_3 = C_4-C_{16}$

This is Reactant D.

EXPERIMENT 7

To 873 parts of Reactant D is added, under good agitation, 127 parts of anhydrous phosphorous pentoxide. The mixture is heated to 85°–100° C. for several hours until the acid values remain essentially unchanged. The resulting product consists of mono- and di-phosphate esters of Reactant D, and is designated Reactant E.

EXPERIMENT 8

To 594 grams of water are added 334 grams of Reactant E, the mixture is agitated and 72 grams of 50% sodium hydroxide are then added. The reactants are heated to 90°–100° C. until 1 part is clear in 9 parts of 20% sodium hydroxide. The product is a clear amber liquid.

EXPERIMENT 9

To 853 parts of Reactant D are added 147 parts of 115% polyphosphoric acid under good agitation. The mixture is then heated to 85°–100° C. for several hours until the acid values remain unchanged. The resulting product consists of mono- and di-phosphate esters of Reactant D, and is designated Reactant F.

EXPERIMENT 10

To 595 parts of water are added 334 parts of Reactant F, then 70 parts of 50% sodium hydroxide are added and the reactants heated to 90°–100° C. until 1 part product is clear in 25% sodium hydroxide. The product is a clear amber liquid.

EXPERIMENT 11

To 266 parts of imidazole derived from caprylic acid and amino-ethylethanolamine are added 475 parts of an ethoxylated alcohol of the general formula $R-O-(CH_2-CH_2O)_xH$; where $R=C_{10}$ and $X=6$. The mixture is agitated and 0.4 parts of a 25% solution of $NaOCH_3$ in alcohol are added. Then 251 parts of ethyl acrylate are added slowly under agitation so that the exotherm does not exceed 45° C. Once all the acrylate is added the mixture is held @ 40°–45° C. for 2 hrs or until a reaction of 85% minimum is reached as determined by an unsaturation test. This then is Reactant G where $R_3=C_6$ and $Y=C_2H_4$.

EXPERIMENT 12

To 1067 parts of Reactant G @ R.T. are added slowly and under good agitation 137 parts of 115% polyphosphoric acid. The mixture is allowed to exotherm from R.T. to 70° C. to facilitate mixing and promote reaction. Once all the PPA is added the temperature is raised to 90°–95° C. and reacted for a few hours until the acid values remain essentially unchanged. This is Reactant H.

EXPERIMENT 13

To 570 parts of water are added 341 parts of Reactant H, the charge is homogenized and 88 parts of 50% sodium hydroxide are added under good agitation. The batch is allowed to exotherm from R.T. to 50° C., but once all the sodium hydroxide is added the batch is heated to 90°–95° C. for several hours or until the product remains clear @ R.T. The pH is then adjusted to 6–7 as is with 85% phosphoric acid. The product is a clear amber liquid.

EXPERIMENT 14

927 parts of Reactant G are mixed and heated with 73 parts of 115% polyphosphoric acid in the same fashion as in Experiment 12. This mixture is then heated with 50% sodium hydroxide in water to produce a mixture as discribed in Experiment 13. This yields a 35% active product.

EXPERIMENT 15

To 801 parts of imidazoline derived from ricinoleic acid and aminoethylethanolamine are added 10 parts of 25% $NaOCH_3$ in methanol, the mixture is homogenized and 189 parts of methyl acrylate are added slowly under good agitation, keeping the batch temp. @ 45° C. max. Once all the acrylate is added the batch is heated for 3 hours @ 40°–45° C. or until 85% min. reaction is obtained via unsaturation test. The product is a clear amber liquid. This is Reactant I where $R_3=C_{16}$ containing an hydroxyl group and a double bond. $Y=C_2H_4$.

EXPERIMENT 16

895 parts of Reactant I are heated to 80° C. and 105 parts of phosphorus pentoxide are added slowly under good agitation, taking care to avoid any sudden exotherm. Once all the $P_2O_5$ has beed added the mixture is heated to 90°–95° C. for several hours until the acid values remain essentially unchanged. This is Reactant J.

EXPERIMENT 17

To 603 parts of water are added 337 parts of Reactant J, the mixture is agitated and then 60 parts of 50% sodium hydroxide are added. Some exotherm develops. Once all the sodium hydroxide has been added the batch was heated to 90°–95° C. for a few hours or until the pH on the as is basis @ R.T. remains unchanged. The batch is cooled to R.T. and adjusted with 50% sodium hydroxide to a pH as is of 9.5–9.8 the product is a clear liquid.

EXPERIMENT 18

To 818 parts of reactant I are added 182 parts of ethyl acrylate, the mixture is heated and refluxed @ 95°–100° C. for several hours until an unsaturation value reveals a minimum of 85% Reaction by residual acrylate. This is Reactant K.

EXPERIMENT 19

To 913 parts of Reactant K are added 87 parts of phosphorous pentoxide under good agitation and heated to 80° C. Once all of the $P_2O_5$ has been added, the batch is heated to 95°–100° C. and held for several hours until the $AV_2$ and AV at pH 7 remain essentially unchanged. The product is a heavy viscous liquid. This is Reactant L.

EXPERIMENT 20

To 593 parts of water are added 340 parts of Reactant L, and the mixture is agitated while heating to 60° C. to homogenize. Once the mixture is clear and homogeneous 6.69 parts of 50% sodium hydroxide are added and the product refluxed for 2 hours or until 1 part product is clear in 9 parts of 25% sodium hydroxide and the pH of a 10% solution is 8–9.0. The product is a clear liquid.

EXPERIMENT 21

To 898 parts of Reactant K are added 102 parts of 115% polyphosphoric acid and heated in the same fashion as in Experiment 19 yielding also a comparable structure to reactant L. This is Reactant M.

EXPERIMENT 22

To 594 parts of water are added 340 parts of Reactant M and 66 parts of 50% sodium hydroxide. The mixture is heated in the same fashion as in Experiment 20 to yield a comparable compound chemically and physically.

EXPERIMENT 23

To 878 parts of Reactant I are added 122 parts of 115% polyphosphoric acid and heated in the same fashion as in Experiment 16 yielding a comparable structure to Reactant J. This is Reactant N.

EXPERIMENT 24

To 604 parts of water are added 337 parts of reactant N and 58 parts of 50% sodium hydroxide, the mixture is heated in the same fashion as in Experiment 17 yielding a comparable product.

EXPERIMENT 25

To 683 parts of castor oil derived imidazoline are added 290 parts of Methyl Acrylate and 27 parts of Acrylic Acid. The mixture is then heated and reacted in the same fashion as in Experiment 1 yielding a comparable product. This is Reactant O where $R_3=C_{16}$ containing an hydroxyl group and a double bond. $Y=C_2H_4$.

EXPERIMENT 26

To 910 parts of Reactant O are added 90 parts of phosphorous pentoxide, and the mixture is treated as in Experiment 2. This is Reactant P.

EXPERIMENT 27

To 595 parts of water are added 337 parts of Reactant P and 68 parts of 50% sodium hydroxide, the mixture is then heated in the same fashion as Experiment 3.

EXPERIMENT 28

Experiment 26 and 27 can be repeated using the proper amounts of Reactant O, 2.7 moles of 115% polyphosphoric acid 1 mole and then the needed amount of sodium hydroxide and water to yield a comparable product to that obtained in Experiment 27.

EXPERIMENT 29

To 810 parts of Reactant O added 190 parts of 115% polyphosphoric acid, the mixture is heated in the same fashion as Experiment 12. This is Reactant Q.

EXPERIMENT 30

To 554 parts of water are added 328 parts of Reactant Q and 118 parts of 50% sodium hydroxide. The mixture is heated in the same fashion as Experiment 13 yielding a clear amber liquid.

EXPERIMENT 31

1 mole of low molecular weight imidazoline (MW=203) is mixed with an equivalent molar amount of methyl acrylate as in Experiment 6 to yield a comparable product. $R=C_3-C_7$ $Y=C_2H_4$.

EXPERIMENT 32

1 mole of isostearic Acid derived imidazoline is treated with an equivalent molar amount of methyl acrylate as in Experiment 6 to yield a comparable product. This product is treated as in Experiment 9 using 115% polyphosphoric acid, and then hydrolyzed as in Experiment 10. $R_3=C_{16}$ $Y=C_3H_6$.

EXPERIMENT 33

To 1 mole of isostearic derived imidazoline are added equivalent mole ratios of methyl acrylate and acrylic acid as in Experiment 1. To this an equivalent molar ratio of phosphorus pentoxide is added as in Experiment 2 and the mixture treated in the same fashion. This product is then converted to the final species by adding the needed amount of water and 50% sodium hydroxide to obtain a 35% active product of the same general formula. $R_3=C_{16}$ $Y=C_2H_4$.

EXPERIMENT 34

To 1 mole of isostearic acid derived imidazoline is added an equivalent mole ratio of methyl acrylate and treated in the same fashion as in Experiment 6. To this is added the molar equivalent of phosphorous pentoxide to prepare and react as per Experiment 7. This product is then converted to the final species by adding the necessary water and 50% sodium hydroxide to prepare a 35% active solution as Experiment 8 yielding a product with the same general structure. $R_3=C_{16}$ $Y=C_2H_4$.

EXPERIMENT 35

To 1 mole of isostearic acid derived imidazoline are added equivalent mole ratios of methyl acrylate and acrylic acid as in Experiment 1. To this is added the molar equivalent of 115% polyphosphoric acid to react as per Experiment 4. This intermediate is then converted to the final product by adding the necessary water and 50% sodium hydroxide to prepare a 35% active product as in Experiment 5, yielding a product with the same general structure.

EXPERIMENT 36

1 mole of stearic acid derived imidazoline is treated in the same fashion as Experiment 32, yielding a product of the same general formula.

EXPERIMENT 37

1 mole of stearic acid derived imidazoline is treated in the same fashion as Experiment 33, to yield a product of the same general formula.

EXPERIMENT 38

1 mole of stearic acid derived imidazoline is treated in the same fashion as Experiment 34, to yield a product of the same general formula.

EXPERIMENT 39

1 mole of stearic acid derived imidazoline is treated in the same fashion as Experiment 35, to yield a product of the same general formula.

EXPERIMENT 40

1 mole of pelargonic acid derived imidazoline is treated in the same fashion as Experiment 32, to yield the desired product. $R_3=C_7$ $Y=C_3H_6$.

EXPERIMENT 41

1 mole of pelargonic acid derived imidazoline is treated in the same fashion as Experiment 33, to yield the desired product. $R_3=C_7$ $Y=C_2H_4$.

EXPERIMENT 42

1 mole of pelargonic acid derived imidazoline is treated in the same fashion as Experiment 34, to yield the desired product. $R_3=C_7$ $Y=C_2H_4OC_2H_4$.

EXPERIMENT 43

1 mole of pelargonic acid derived imidazoline is treated in the same fashion as Experiment 35, to yield the desired product. $R_3=C_7$ $Y=C_2H_4$.

EXPERIMENT 44

1 mole of caprylic acid derived imidazoline is treated in the same fashion as Experiment 32, to yield the desired product. $R_3=C_6$ $Y=C_2H_4$.

EXPERIMENT 45

1 mole of caprylic acid derived imidazoline is treated in the same fashion as Experiment 33, to yield the desired product. $R_3=C_6$ $Y=C_2H_4OC_2H_4$.

EXPERIMENT 46

1 mole of caprylic acid derived imidazoline is treated in the same fashion as Experiment 34, to yield the desired product. $R_3=C_6$ $Y=C_3H_6$.

EXPERIMENT 47

1 mole of caprylic acid derived imidazoline is treated in the same fashion as Experiment 35, to yield the desired product. $R_3=C_6$ $Y=C_2H_4$.

EXPERIMENT 48

To 795 parts of coco derived imidazoline, are added 205 parts of acrylamide. The mixture is heated to 95° C. for several hours until 85% reaction is achieved as determined by an unsaturation test. The product exhibits the following probable structure:

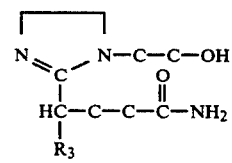

$R = C_4-C_{16}$

This is Reactant R.

EXPERIMENT 49

847 parts of Reactant R are heated to 90° C. and 153 parts of 115% polyphosphoric acid are added slowly under good agitation allowing the temperature to drop down to 75° C. Once all the polyphosphoric acid has been added the mixture is heated to 95° C. for several hours until the acid values remain essentially unchanged. The resulting product consists of mono- and di-phosphate esters of Reactant R, and is designated Reactant S.

EXPERIMENT 50

To 330 parts of Reactant S are added 598 parts of water, and the mixture is heated to 55° C. and agitated to produce a homogeneous solution. To the solution 72 parts of 50% sodium hydroxide are added under good agitation and the total mixture is then heated to 90° C., making sure to control foam in the reaction vessel. The mixture is heated for two hours or until 1 part product is clear in 9 parts of 20% sodium hydroxide. The resulting product is clear, yellow liquid.

EXPERIMENT 51

To 617 parts of coco-derived imidazoline are added 224 parts of ethyl acrylate and 159 parts of acrylamide. The mixture is heated to 90°-95° C. for several hours until 85% reaction is obtained as determined by an unsaturation test. The product exhibits the following structure:

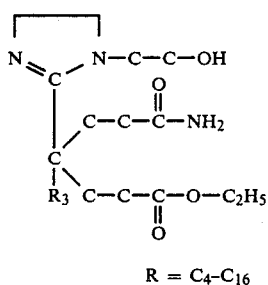

R = C$_4$-C$_{16}$

This is Reactant T.

EXPERIMENT 52

877 parts of Reactant T are heated to 80° C. and 123 parts of 115% polyphosphoric acid are added slowly under good agitation. The mixture is then heated to 90°-95° C. until the acid values remain essentially unchanged. The resulting product consists of mono- and di-phosphate esters of Reactant T, and is designated Reactant U.

EXPERIMENT 53

To 587 parts of water are added 335 parts of Reactant U. The mixture is heated to 60° C. to homogenize and then 80 parts of 50% sodium hydroxide are added under good agitation. The mixture is then heated to 95°-100° C. until 1 part product is clear in 9 parts of 35% sodium hydroxide. The resulting product is a clear, yellow liquid.

EXPERIMENT 54

895 parts of Reactant T are heated to 80°-85° C. and 105 parts of anhydrous phosphorous pentoxide are added slowly over a one hour period under good agitation. The mixture is then heated to 95° C. for several hours until the acid values remain essentially unchanged. This product exhibits a structure similar to that of Experiment 52. This is reactant V.

EXPERIMENT 55

To 577 parts of water are added 343 parts of Reactant V, the mixture is heated to 55° C. to homogenize and then 80 parts of 50% sodium hydroxide are added under good agitation. The mixture is heated at 90°-95° C. for several hours until 1 part product is clear in 9 parts of 35% sodium hydroxide. Product exhibits a structure similar to that of Experiment 53.

EXPERIMENT 56

To 660 parts of coco-derived imidazoline are added 340 parts of acrylamide. The mixture is heated to 95° C. and reacted for several hours until at least 85% reaction is achieved as determined by an unsaturation test. The product exhibits the following probable structure:

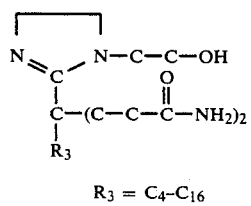

R$_3$ = C$_4$-C$_{16}$

This is Reactant W.

EXPERIMENT 57

To 285 parts of Reactant W are added 43 parts of 115% polyphosphoric acid, and the mixture is treated as in Experiment 52. To this then is added 592 parts of water and homogenized at 45° C., then 81 parts of 50% sodium hydroxide are added and heated at 95° C. until 1 part product is clear in 9 parts of 30% sodium hydroxide. Product exhibits a similar structure to that of Experiment 53.

EXPERIMENT 58

To 290 parts of Reactant W are added 36 parts of anhydrous phosphorous pentoxide at 80°-85° C. over a one hour period. The mixture is then heated at 95° C. for several hours in the same fashion as Reactant V. To this then is added 591 parts of water and the mixture is agitated at 35° C. until it is homogeneous. Then 82 parts of 50% sodium hydroxide are added and the mixture is heated @ 95° C. until 1 part product is clear in 9 parts of 30% sodium hydroxide. Product exhibits a similar structure to that of Experiment 53.

USES

The products of this invention exhibit a wide range of surfactant properties thus rendering these materials useful in a wide range of applications; these include:

Cosmetics: formulation of shampoos, bubble baths, deodorants, antiperspirant sticks, creams and lotions, hair conditioners, foaming bath oils, hair dyes, hair dressings, corrosion inhibitors and skin care products.

Textiles: laundry detergents, fabric softeners, rug and upholstery cleaners, fiber lubricants, antistats, dyeing assistants, fulling agents, bleaching, desizing, mercerizing.

Metal Cleaners: ferrous and nonferrous metals, alkaline cleaners, acid cleaners, soak tank cleaners, spray cleaners, degreasers, aircraft cleaners, railroad car cleaners, truck and bus cleaners, car washes.

Metal Working Fluids: cutting oils, rolling oils, drawing compounds, chain lubricants, grinding compounds, burnishing compounds, corrosion inhibition and extreme pressure lubricants.

Petroleum: secondary, tertiary and recovery emulsion breakers, drilling fluids, corrosion inhibitors, gasoline and fuel additives, scale inhibition.

Paper: wood pulping, pitch dispersnats, de-inking, rewetting, felt washing, pigment dispersing, antistatic and leveling agents.

Paints: dispersants, wetting agents, defoamers, corrosion inhibitors.

Plastics and Resins: emulsion polymerization, suspension polymerizaization, antistatic agents, mold release agents, lubricants.

In addition to the high solubility and stability exhibited by these novel products in acid and alkaline systems they function as excellent hydrotropes in high electrolyte systems as shown by the following examples.

| HYDROTROPIC PROPERTIES | |
|---|---|
| A. Sodium m-Silicate Anhydrous | 6.0% |
| Product from EXPERIMENT 3 | 1.0% |
| Surfonic N-95 (Jefferson Chemical Co.) | 4.0% |
| Water | Q.S. to 100 |
| Cloud Point with Product from EXPERIMENT 3 | >80° C. |
| Cloud Point without Product from | 14° C. |

| HYDROTROPIC PROPERTIES | |
|---|---|
| EXPERIMENT 3 | |
| B. Sodium m-Silicate Anhydrous | 2.6% |
| Sodium Carbonate | 1.7% |
| Tetra Sodium Pyrophosphate | 1.3% |
| Igepal CO-710 (GAF) | 1.2% |
| Product from EXPERIMENT 3 | 1.0% |
| Water | Q.S. to 100 |
| Cloud Point with Product from EXPERIMENT 3 | >80° C. |
| Cloud Point without Product from EXPERIMENT 3 | 30° C. |

What is claimed is:

1. A phosphobetaine compound of the formula

wherein

A is selected from OH, OM AND OYR

B selected from OH and OM

R is an imidazoline reactant moiety of the formula

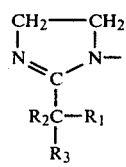

wherein $R_3$ is alkyl, alkenyl, alkoxy, hydroxyalkyl or hydroxyalkenyl of from 2 to 20 carbon atoms each or aryl or alkylaryl or cycloaliphatic of up to 20 carbon atoms, $R_1$ and $R_2$ are individually selected from hydrogen, propionic acid, propionitrile, propionamide, propionate esters of $C_1$-$C_{12}$ alkyl, alkylaryl or alkylcycloaliphatic or alkali metal or alkaline earth metal salts or amine salts of propionic acid with the proviso that at least one of $R_1$ and $R_2$ must be a propionate derivative, Y is alkylene of 2 to 6 carbon atoms optionally interrupted by up to 3 oxygen atoms, of up to 12 carbon atoms, M is selected from alkali metals, alkaline earth metals and amines.

2. Phosphobetaine compound as claimed in claim 1 of the formula

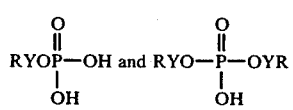

wherein $R_1$=CH$_2$CH$_2$CO$_2$CH$_3$ $R_2$=H

R, $R_3$ and Y are defined as before.

3. Phosphobetaine compound as claimed in claim 1 of the formula

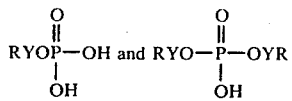

wherein $R_1$=$R_2$=CH$_2$CH$_2$CO$_2$CH$_3$

R, $R_3$ and Y are defined as before.

4. Phosphobetaine compound as claimed in claim 1 of the formula

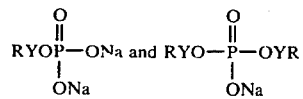

wherein $R_1$=CH$_2$CH$_2$CO$_2$Na, $R_2$=H

R, $R_3$ and Y are defined as in claim 1.

5. Phosphobetaine compound as claimed in claim 1 of the formula

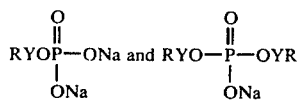

where $R_1$=$R_2$=CH$_2$CH$_2$CO$_2$Na

R, $R_3$ and Y are defined as in claim 1.

6. Phosphobetaine compound as claimed in claim 1 of the formula

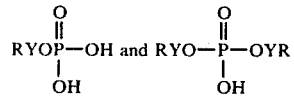

wherein $R_1$=CH$_2$CH$_2$CONH$_2$, $R_2$=H

R, $R_3$ and Y are defined as in claim 1.

7. Phosphobetaine compound as claimed in claim 1 of the formula

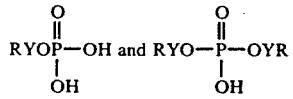

wherein $R_1$=$R_2$=CH$_2$CH$_2$CONH$_2$

R, $R_3$ and Y are defined as in claim 1.

8. Phosphobetaine as in claim 2 wherein $R_3$=$C_4$-$C_{16}$.

9. Phosphobetaine as in claim 2 wherein $R_3$=$C_4$-$C_{16}$ and Y is $C_2H_4$.

10. Phosphobetaine as in claim 3 wherein $R_3$=$C_4$-$C_{16}$.

11. Phosphobetaine as in claim 3 wherein $R_3$=$C_4$-$C_{16}$ and Y is $C_2H_4$.

12. Phosphobetaine as in claim 4 wherein $R_3$=$C_4$-$C_{16}$.

13. Phosphobetaine as in claim 4 wherein $R_3$=$C_4$-$C_{16}$ and Y is $C_2H_4$.

14. Phosphobetaine as in claim 5 wherein $R_3$=$C_4$-$C_{16}$.

15. Phosphobetaine as in claim 5 wherein $R_3 = C_4-C_{16}$ and Y is $C_2H_4$.

16. Phosphobetaine as in claim 4 wherein $R_3$ is a straight chain $C_{16}$ alkyl and Y is $C_2H_4$.

17. Phosphobetaine as in claim 5 wherein $R_3$ is a straight chain $C_{16}$ and Y is $C_2H_4$.

18. Phosphobetaine as in claim 4 wherein $R_3$ is a branched chain $C_{16}$ and Y is $C_2H_4$.

19. Phosphobetaine as in claim 5 wherein $R_3$ is a branched chain $C_{16}$ and Y is $C_2H_4$.

20. Phosphobetaine as in claim 4 wherein $R_3$ is an unsaturated straight chain $C_{16}$ and Y is $C_2H_4$.

21. Phosphobetaine as in claim 5 wherein $R_3$ is an unsaturated straight chain $C_{16}$ and Y is $C_2H_4$.

22. Phosphobetaine as in claim 4 wherein $R_3$ is a hydroxy substituted $C_{16}$ saturated or unsaturated chain and Y is $C_2H_4$.

23. Phosphobetaine as in claim 5 wherein $R_3$ is a hydroxy substituted $C_{16}$ saturated or unsaturated chain and Y is $C_2H_4$.

* * * * *

UNITED STATES PATENT AND TRADEMARK OFFICE
CERTIFICATE OF CORRECTION

PATENT NO. : 4,490,536
DATED : Dec. 25, 1984
INVENTOR(S) : Miguel Corti, et al.

It is certified that error appears in the above-identified patent and that said Letters Patent is hereby corrected as shown below:

Column 1, line 44, "R" should be -- $R_3$ --.

Signed and Sealed this

Twentieth Day of August 1985

[SEAL]

Attest:

DONALD J. QUIGG

Attesting Officer     Acting Commissioner of Patents and Trademarks